(12) United States Patent
Nosky et al.

(10) Patent No.: US 6,890,541 B1
(45) Date of Patent: May 10, 2005

(54) METHOD FOR ENHANCING PRODUCTION PERFORMANCE IN AN ANIMAL

(75) Inventors: Bruce J. Nosky, Hull, GA (US);
Robert E. Pitts, Athens, GA (US);
Dragan R. Rogan, London (CA)

(73) Assignee: Bioniche Life Sciences, Inc., Belleville (CA)

( * ) Notice: Subject to any disclaimer, the term of this patent is extended or adjusted under 35 U.S.C. 154(b) by 116 days.

(21) Appl. No.: 10/031,752

(22) PCT Filed: Jul. 21, 2000

(86) PCT No.: PCT/US00/20013

§ 371 (c)(1),
(2), (4) Date: Jan. 23, 2002

(87) PCT Pub. No.: WO01/07080

PCT Pub. Date: Feb. 1, 2001

Related U.S. Application Data

(60) Provisional application No. 60/145,314, filed on Jul. 23, 1999.

(51) Int. Cl.$^7$ .................. A61K 39/04; A61K 45/00; A61K 47/00
(52) U.S. Cl. .................. 424/248.1; 424/278.1; 424/282.1
(58) Field of Search .................. 424/248.1, 278.1, 424/282.1

(56) References Cited

U.S. PATENT DOCUMENTS

| | | | |
|---|---|---|---|
| 4,744,984 A | 5/1988 | Ragland | |
| 5,632,995 A | 5/1997 | Wade et al. | |
| 5,759,554 A | 6/1998 | Alkemade et al. | |

FOREIGN PATENT DOCUMENTS

| | | |
|---|---|---|
| WO | WO 94/16727 | 8/1994 |
| WO | WO 95/05837 | 3/1995 |
| WO | WO 98/24327 | 6/1998 |

OTHER PUBLICATIONS

Forsthuber, Thomas et al., "Induction of $T_H1$ and $T_2 2$ Immunity in Neonatal Mice," Science, vol. 271, pp. 1728–1730, Mar. 22, 1996.

Griebel et al., "Ontogeny of the Immune Response: Effect of Protein Energy Malnutrition in Neonatal Calves," Can J Vet Res, 1987, pp. 428–435, vol. 51.

Hauser et al., "Variation of neutrophil function with age in calves," Am J Vet Res, Jan., 1986, pp. 152–153, vol. 47, No. 1.

Radostits et al., "A Textbook of Health and Production Management of Agricultural Animals," Herd Health, 1985, pp. 116–132, W.B. Saunders Company, Philadelphia, PA.

Renshaw et al., "Levels of total haemolytic complement activity in paired dairy cow–newborn calf sera," Immunology, 1978, pp. 801–805, vol. 34, Blackwell Scientific Publications.

Rossi et al., "Evidence for Suppression or Incomplete Maturation of Cell–Mediated Immunity in Neonatal Calves as Determined by Delayed–Type Hypersensitivity Responses," Am J Vet Res, Aug., 1981, pp. 1369–1370, vol. 42, No. 8.

Rossi et al., "Kinetics of Detection of Blastogenic Responses of Neonatal Calves Inoculated in Utero with Tetanus Toxoid, Killed Mycobacterium bovis, and Killed Brucella abortus," Am J Vet Res, Apr., 1979, pp. 576–579, vol. 40, No. 4.

"The Science Behind Immunoboost®," Jun. 2, 2001, pp. 1–3; "Technical Report—Immunoboost®—*E. coli* Challenge Study," pp. 1–2; and "Features and Benefits—Features of Immunoboost®," p. 1, <URL: http://www.vetrepharm.com/immuno.science.htm>.

Van Kampen, "Immunotherapy and Cytokines," Seminars in Veterinary Medicine and Surgery (Small Animal), Aug., 1997, pp. 186–192, vol. 12, No. 3, W.B. Saunders Company.

Woodard et al., "Cell–Mediated Immune Responses of Neonatal Calves and Adult Cattle Following Inoculation with PPD of Mycobacterium bovis Associated with a Mycobacterial Immunopotentiating Glycolipid and Oil Droplets," Am J Vet Res, May, 1979, pp. 636–644, vol. 40, No. 5.

*Primary Examiner*—Mark Navarro
(74) *Attorney, Agent, or Firm*—Kilpatrick Stockton LLP

(57) ABSTRACT

The present invention provides methods for activating the immune systems of newborn animals and methods for enhancing the production performance of the animals. More particularly, the methods of the present invention involve the administration of compositions comprising mycobacterial cell wall extract, most preferably cell wall extracts of *Mycobacterium phlei*.

36 Claims, 5 Drawing Sheets

METHOD FOR ENHANCING PRODUCTION PERFORMANCE IN AN ANIMAL

CROSS-REFERENCE TO RELATED APPLICATIONS

This application is a 371 national phase application of PCT/US00/20013, filed Jul. 21, 2000 which claims benefit of U.S. Provisional Application Ser. No. 60/145,314 filed Jul. 23, 1999.

TECHNICAL FIELD

The present invention relates to a method for activating the immune system in a newborn animal and for enhancing production performance of the animal.

BACKGROUND OF THE INVENTION

An increase in the average daily weight gain of an animal is of great importance to enterprises where the body weight of the animal is necessary for the commercial success of the enterprise. Weight gain also is important for animals, including humans, who have lost weight due to a disease, a mental disorder or a medical treatment.

Attempts to enhance production performance in domestic food animals have largely focused on the use of feed efficiency enhancers including, but not limited to, formulations containing nutrients, vitamins, minerals, hormones, sulphonomides, antiprotozoals, antifungals, antivirals, antiparasitics, antibiotics and vaccines.

Hormones including, but not limited to estrogens, estradiol, progesterone, synthetic progestins, testosterone, anabolic steroids and somatotrophin production stimulants are expensive and should not be used in breeding animals. In addition, their use in food animals is unacceptable to large segments of the population and is restricted in some countries. Antiprotozoals, antifungals, antivirals, antiparasitics and antibiotics including, but not limited to, terramycin, tetracycline, virginiamycin, aureomycin and lincomycin are expensive, can be toxic to humans and cannot be used in all animal species. There is public concern regarding the overuse and misuse of antibiotics in animal husbandry, leading to development of antibiotic resistant organisms. Again, their use in food animals is unacceptable to large segments of the population and is restricted in some countries. Vaccines, used to combat specific infectious diseases in domestic food are expensive, are not available for all diseases and can result in selection of pathogenic organisms for virulency and for resistance.

Various biological and chemical immunomodulators have been used to stimulate the immune system to minimize the impact of disease in animals, including humans. These include, but are not limited to, opiod peptides, thymosins, glucocorticoids, cytokines, interferons, levamisole, isoprinosine, poynucleotides and microbial products. Microbial products that have been used as immunomodulators include, but are not limited to, heat killed or formaldehyde treated suspensions of *Priopionibacterium acnes*, microbial polysaccharides, lipopolysaccharides, protein-bound polysaccharides, muramyl-dipeptide, lipid A and *Mycobacterium phlei* cell wall extract (U.S. Pat. No. 4,744,984; U.S. Pat. No. 5,759,554).

Domestic food animals are particularly susceptible to infectious disease during the first year of life and more particularly during the neonatal period. Among calves over 70% of deaths that occur during the first year of life occur during the neonatal period when their immune system is functionally immature (Radostits et al. 1985. Herd Health W. B. Saunders, Philadelphia Pa. pgs. 116–1400). Functional immaturity of the immune system includes, but is not limited to, sub-optimal neutrophil function (Hauser et al. 1986. Am. J. Vet. Res. 47:152–153), decreased complement activity (Renshaw et al. 1978. Immunology 34:801–805), poor induction of delayed hypersensitivity reactions (Woodward et al. 1979. Am. J. Vet. Res. 40:636–644), low levels of interleukin (IL)-2 production (Griebel et al. 1987. Can. J. Vet. Res. 51:428–435) and weak lymphocyte proliferative responses (Rossi et al. 1979. Am. J. Vet. Res. 40:576–579; Rossi et al. 1981. Am. J. Vet Res. 27:1369–1370).

Because of the many diseases to which animals are vulnerable and because, during the newborn and neonatal periods, some of these diseases are exacerbated by an immature immune system, there is a need for a novel method for activating the immune system to enhance disease resistance, especially during the newborn and neonatal periods, and, thereby, to increase production performance in these animals.

This method should be relatively inexpensive to prepare, easy to administer and suitable for use in all animals. Moreover, its activity should remain stable over time, be reproducible among preparations, be effective at dose regimens associated with minimal toxicity, be safe for the consumer and be acceptable to all segments of the population.

SUMMARY OF THE INVENTION

The present invention satisfies the above needs by providing a method for activating the immune system of a newborn animal to enhance production performance of the animal comprising administering to the newborn animal an effective amount of MCWE, thereby activating the immune system of the newborn animal to enhance production performance. More particularly, the present invention provides a method for activating the immune system of a newborn animal to enhance production performance of the animal comprising administering to the newborn animal within 24 hours of birth an effective amount of MCWE, thereby activating the immune system of the newborn animal to enhance production performance.

The present invention provides a method of activating the immune system of a newborn animal and enhancing production performance of the animal comprising administering to the newborn animal an effective amount of a *Mycobacterium phlei* cell wall extract (MCWE), thereby activating the immune system of the animal and enhancing production performance of the animal.

More particularly, the present invention satisfies the above needs by providing a method, wherein a composition comprising MCWE and a pharmaceutically acceptable carrier is administered to an animal within 24 hours of birth in an amount effective to activate the immune system of the animal and to enhance production performance of the animal. MCWE is relatively inexpensive to prepare, easy to administer, suitable for use in all animals including, but not limited to, domestic food animals, safe for the consumer and acceptable for use to all segments of the population and in all countries. Its activity is reproducible among preparations and remains therapeutically stable over time. It is effective at dose regimens that are associated with minimal toxicity even upon repeated administration and it has few or no side-effects. The unexpected ability of MCWE to stimulate the immune system of an animal during the newborn and neonatal periods and to enhance production performance of the animal provides important benefits for, among others, the domestic animal food industry and the consumer of domestic animal products.

Although not wanting to be bound by the following hypothesis, it is thought that MCWE, when administered within 24 hours of birth, activates maturation of the animals immature immune system and, by enabling the animal to better resist opportunistic infectious agents and to better withstand stress both during and after the newborn and neonatal periods, enhances production performance. It is to be understood that administration of MCWE is not a specific immunization process, but is a method for nonspecifically activating maturation of the immature immune system of the animal and, perhaps also, for increasing the animal's metabolism so as to enhance production performance.

Accordingly, it is on object of the present invention to provide a method for activating maturation of the immature immune system in a newborn animal.

Another object of the present invention is to provide a method for protecting an animal from opportunistic infectious agents during the newborn and neonatal periods.

Another object of the present invention is to provide a method for protecting an animal from opportunistic infectious agents after the newborn and neonatal periods.

Another object of the present invention is to provide a method for enabling an animal to better withstand stress during the newborn and neonatal periods.

Another object of the present invention is to provide a method for enabling an animal to better withstand stress after the newborn and neonatal periods.

Another object of the present invention is to provide a method for protecting an animal from diseases exacerbated by stress during the newborn and neonatal periods.

Another object of the present invention is to provide a method for protecting an animal from diseases exacerbated by stress after the newborn and neonatal periods.

Another object of the present invention is to provide a method for enabling the survival of an animal during the newborn and neonatal periods.

Another object of the present invention is to provide a method for enabling the survival of an animal after the newborn and neonatal periods.

Another object of the present invention is to provide a method for increasing metabolism of an animal during the newborn and neonatal periods.

Another object of the present invention is to provide a method for increasing metabolism of an animal after the newborn and neonatal periods.

Another object of the present invention is to provide a method for increasing the efficiency of feed use in an animal during the newborn and neonatal periods.

Another object of the present invention is to provide a method for increasing the efficiency of feed use in an animal after the newborn and neonatal periods.

Another object of the present invention is to provide a method for enhancing production performance in an animal during the newborn and neonatal periods.

Another object of the present invention is to provide a method for enhancing production performance in an animal after the newborn and neonatal periods.

Another object of the present invention is to provide a method for enhancing production performance in an animal that is not toxic.

Another object of the present invention is to provide a method for enhancing production performance in an animal that is not carcinogenic.

Another object of the present invention is to provide a method for enhancing production performance in an animal that is not teratogenic.

Another object of the present invention is to provide a method for enhancing production performance in an animal that is safe for use in all animal species.

Another object of the present invention is to provide a method for enhancing production performance in an animal that is safe for the consumer.

Another object of the present invention is to provide a method for enhancing production performance in an animal that is acceptable to the consumer.

Another object of the present invention is to provide a method for enhancing production performance in an animal using a composition that can be prepared in large amounts.

Another object of the present invention is to provide a method for enhancing production performance in an animal using a composition that is relatively inexpensive to prepare.

Another object of the present invention is to provide a method for enhancing production performance in an animal using a composition that remains stable over time.

Another object of the present invention is to provide a method for enhancing production performance in an animal that can be used with hormonal agents.

Another object of the present invention is to provide a method for enhancing production performance in an animal that can be used with other pharmaceutical agents.

Another object of the present invention is to provide a method for enhancing production performance in an animal that can be used with vaccines.

These and other objects, features and advantages of the present invention will become apparent after a review of the following detailed description of the disclosed embodiment and the appended claims.

DETAILED DESCRIPTION OF THE INVENTION

Figure 1A:
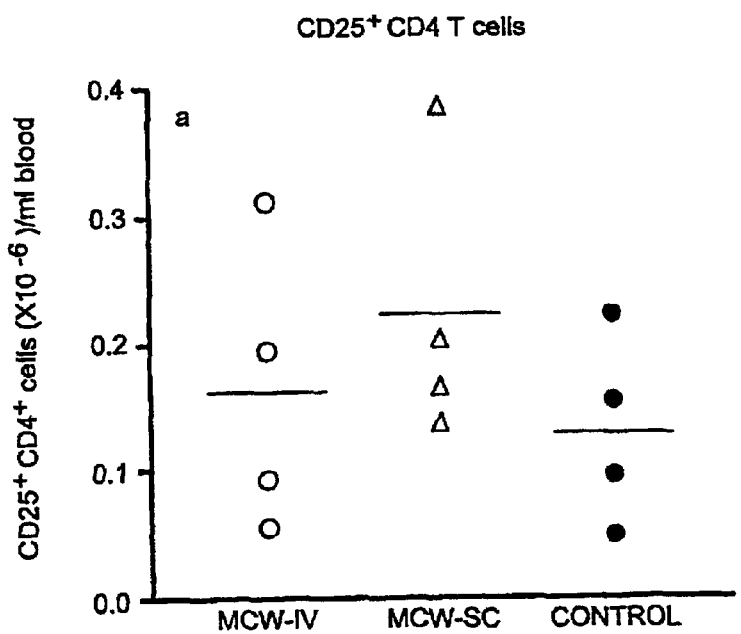
FIG. 1. $CD25^+CD4^+$ T-lymphocytes/ml (A) and MHC Class $II^+CD4^+$ T-lymphocytes/ml (B) in blood obtained on day 4 from calves treated within 24 h of birth (day 0) with MCWE-IV, MCWE-SC and saline-SC (control). Values are for individual animals and bars represent mean values for each group (n=4).

The present invention provides a method for activating the immune system of a newborn animal to enhance production performance of the animal comprising administering to the newborn animal an effective amount of MCWE, thereby activating the immune system of the newborn animal to enhance production performance. More particularly, the present invention provides a method for activating the immune system of a newborn animal to enhance production performance of the animal comprising administering to the newborn animal within 24 h of birth an effective amount of MCWE, thereby activating the immune system of the newborn animal to enhance production performance.

As used herein, the term "newborn period" includes birth to 96 hours after birth.

As used herein, the term "neonatal period" includes birth to 28 days after birth.

As used herein, the term "immature immune system" includes functional deficiencies of the white blood cells of the immune system.

As used herein, the term "production performance" includes the average daily weight gain of an animal, the mortality of an animal, the number of treatment days necessary to maintain the health of an animal, the cost of treatment necessary to maintain the health of an animal and any combination thereof.

As used herein, the term "enhance production performance" includes an increase in the average daily weight gain of an animal, a decrease in the mortality of an animal, a decrease in the number of treatment days necessary to maintain the health of an animal, a decrease in the cost of treatment necessary to maintain the health of an animal and any combination thereof.

As used herein, the term "pharmaceutical agent" includes any natural or synthetic agent approved by a regulatory agency of a country or a state government or listed in the U.S. Pharmacopoeia (USP) or other generally recognized pharmacopoeia for use in an animal, including a human.

As used herein, the term "domestic food animal" includes any animal that is raised commercially for use as food or in food.

MCWE and a pharmaceutically acceptable carrier are prepared by uniformly and intimately bringing into association the MCWE with liquid carriers, with solid carriers, or with both. Liquid carriers are aqueous carriers and non-aqueous carriers. These include, but are not limited to, aqueous suspensions, oil emulsions, water in oil emulsions, water-in-oil-in-water emulsions, site-specific emulsions, long-residence emulsions, sticky-emulsions, microemulsions, nanoemulsions and liposomes. Solid carriers are biological carriers and chemical carriers. These include, but are not limited to, microparticles, microspheres, nanospheres, nanoparticles, minipumps and natural and synthetic polymers that allow for sustained release of the MCWE. Further, MCWE can be used with any one, all, or any combination of excipients regardless of the carrier used to present the composition to the responding cells. These include, but are not limited to, anti-oxidants, buffers, and bacteriostats, and may include suspending agents and thickening agents.

For example, MCWE is suspended in a pharmaceutically acceptable carrier such as, but not limited to, water, saline or phosphate buffered saline (PBS) and is sonicated. Optionally, the sonicated mixture is emulsified by microfluidization. In an embodiment, lyophilized MCWE is mixed with sterile saline and is sonicated at 20% output for 5 minutes (Model L2015 Sonicator, Heat Systems-Ultrasonics Inc) and, optionally, the sonicated mixture is emulsified by microfluidization at 15,000–30,000 psi for one flow-through (Model M-110Y; Microfluidics, Newton, Mass.). The mixture is either aseptically processed or terminally sterilized.

For example, MCWE is mixed with a mineral oil or with a neutral oil including, but not limited to, a diglyceride, a triglyceride, a phospholipid, a lipid, an oil and mixtures thereof, wherein the oil contains an appropriate mix of polyunsaturated and saturated fatty acids. Examples include, but are not limited to, squalane, squalene, n-hexadecane and to soybean oil, canola oil, palm oil, olive oil and myglyol, wherein the number of fatty acid carbons is between 12 and 22 and wherein the fatty acids can be saturated or unsaturated. Optionally, charged lipid or phospholipid can be suspended in the neutral oil. In an embodiment, phosphatidylcholine and triglyceride soybean oil are dissolved by gentle heating at 50°–60° C. Lyophilized MCWE is added, the mixture is incubated for 60 min. at 20° C. and PBS is added. The mixture is sonicated at 20% output for 5 min and, optionally, is emulsified by microfluidization at 15,000–30,000 psi for one flow-through. The mixture is either aseptically processed or terminally sterilized.

It will be understood by those skilled in the art there are many methods for suspending the MCWE in its pharmaceutically acceptable carrier. Numerous variations of aqueous carrier and of oil and aqueous carrier, of proportions and of emulsification means will be apparent to those skilled in the art and can be used with MCWE in practicing the present method. Optionally, antibiotics including, but not limited to, gentamycin and amphoteracin B can be added as a preservative to the MCWE emulsion. The preferred concentration of gentamycin is between about 10 $\mu$g/ml and about 50 $\mu$g/ml and of amphoteracin B is between about 0.5 $\mu$g/ml to about 5 $\mu$g/ml.

Animals whose immature immune system can be activated by MCWE and whose production performance can be enhanced by MCWE include, but are not limited to, newborn mammals, birds, fish, amphibians and crustaceans. Preferably the animals are newborn mammals, birds and fish, more preferably newborn mammals and birds. Mammals include, but are not limited to, newborn cattle, horses, pigs, sheep, goats, reindeer, elk, fallow deer, bison, dogs, cats and humans. Birds include, but are not limited to, newborn chickens, ducks, geese, turkeys and quails.

Routes of administration include, but are not limited to, oral, intravenous (IV), subcutaneous (SC), intramuscular (IM), intraperitoneal, intradermal, intraocular, intrapulmonary, transdermal, subdermal, topical, mucosal, nasal and impression into skin. Preferably, the MCWE is administered orally, IV, SC or IM.

MCWE is administered to a newborn animal at a time and in an amount effective to activate the immature immune system in the animal and to enhance production performance of the animal. The time is preferably from 1 h of age to 28 day of age, more preferably from 1 hour of age to 4 days of age and most preferably from 1 hour of age to 24 hours of age. The amount of MCWE administered will depend on the animal being treated, the time of administration, the route of administration and other factors such as the species, size and weight of the animal. Preferably, the dose of MCWE administered is from about 0.001 $\mu$g/kg to about 600 $\mu$g/kg per dose, more preferably from about 0.01 µg/kg to about 400 µg/kg per dose, and most preferably from about 0.1 µg/kg to about 200 µg/kg per dose. Depending on the route of administration, the volume per dose is preferably about 0.01 ml to about 50 ml per dose, more preferably about 0.1 ml to about 25 ml and most preferably about 0.5 ml to about 10 ml. The MCWE can be administered in a single dose or in multiple doses over a period of time and on a schedule appropriate to the animal being treated and the route of administration. The amount of MCWE administered is preferably between about 1 mg and 1000 mg, more preferably between about 25 mg and 500 mg and most preferably between about 50 mg and 300 mg.

The following examples will serve to further illustrate the present invention without, at the same time, however, constituting any limitation thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLE 1
MCWE Emulsion

MCWE was prepared as in U.S. Pat. No. 4,744,984, which is incorporated by reference herein. Briefly, *Mycobacterium phlei* were grown in liquid medium and harvested, the bacteria were disrupted, the cell walls collected, deproteinized, delipidated, washed, and lyophilized. MCWE can be obtained commercially from Bioniche Life Sciences, Inc. (London, Ontario, Canada). For use, lyophilized MCWE was emulsifed in:

TABLE 1

| MCWE Emulsion | |
|---|---|
| COMPONENT | FINAL CONCENTRATION |
| Lyophilized MCWE | 0.1 g |
| Squalane | 2% |
| Polysorbate (Tween)-80 | 0.2 g |
| Phosphate buffened saline, pH 7.2 | QS to 100 ml |
| Gentamycin | 3.0 mg |

MCWE was added to a dry, sterile beaker. Squalane was added and the mixture was covered and allowed to sit overnight. The mixture was brought to 100 ml with sterile, phosphate buffered saline containing 80% polyoxyethylenesorbitan monooleate, Tween 80. The optimum concentration of oil in the oil and water mixture is between approximately 1% and 7%. The mixture was emulsified using a Microfluidics tabletop microfluidizer Model M-110Y at 10,700–23,000 psi for one flow-through. Sterile glass vials were filled with 5 and 20 ml of the MCWE emulsion under sterile laminar air flow using a Filamatic Vial Filler (National instrument Co., Baltimore, Md.). The glass vials were capped, sealed and stored at 4° C.

EXAMPLE 2
Activation of the Immature Immune System by MCWE

Clinically healthy, colostrum-deprived calves of domestic cows were obtained within 8 hours of birth. The calves were placed in individual pens within an open shelter, fed twice daily with fresh milk containing no antibiotics and subjected to the same routine ranch practices. No medications or vaccinations, other than MCWE, were administered during the study period.

Fifteen newborn calves were randomly divided into 3 groups. Within 24 hours of birth, Group 0 calves received 250 µg of MCWE in 1 ml of emulsion IV, Group 2 calves received 250 µg of MCWE in 1 ml of emulsion SC and Group 3 calves received 1 ml saline SC.

Body temperature, behavior, milk consumption and fecal consistency were assessed twice a day and scored on a scale of 0 (normal) to 3 (severe symptoms). Hydration was assessed twice a day and scored on a scale of 0 (normal) to 2 (severe dehydration). Animals having a score of <1 were considered as clinically normal. Animals having a score of >1 were considered as clinically abnormal and were excluded from the study analyses.

Blood, obtained from each animal prior to MCWE administration, was analyzed for white blood cells (WBCs) and for interferon gamma (IFNγ). In addition, two zinc sulphate turbidity tests were performed to confirm that transfer of maternal antibodies had not occurred. Blood, obtained from each animal on days 1–4 post-MCWE administration, was analyzed for WBCs and for IFNγ.

WBC counts were determined using a CELL-DYN 3500 R ANALYZER® (Abbott Laboratories, Irving TX) and Sheath Reagent (WIC/HGB Lyse Diluent). Differential WBC counts were determined on Wright's stained blood smears. Whole blood was lysed in ammonium chloride solution to generate a population of peripheral blood leukocytes (PBLs) that included monocytes, lymphocytes and polymorphonuclear leukocytes (PMNs). Flow cytometry was used to analyze lymphocyte and monocyte subpopulations using the antibodies listed in Table 2. Electronic gates based on forward angle and right angle light scatter were used to exclude PMNs from the flow cytometric analysis.

TABLE 2

| Monoclonal Antibodies | | |
|---|---|---|
| Clone Number | Antigen Specificity | Cell Type Identified |
| MM1A | CD3 | T-lymphocyte |
| Pig45A | Surface IgM | B-lymphocyte |
| DH59B | Mononuclear Cells | Monocyte |
| IL-AII | CD4 | $CD4^+$ T-lymphocyte |
| CACT116A | CD25 | $CD25^+CD4^+$ T-lymphocyte |
| TH14B | MHC Class II | MHC Class $2^+CD4^+$ T-lymphocyte |

Single labeling was detected using FITC-conjugated goat-anti-mouse IgG. Dual labeling was detected using FITC-conjugated goat-anti-mouse IgG and PE-conjugated, isotype-specific goat anti-mouse Ig. Flow cytometric analyses were performed using a FACSSCAN® flow cytometer and the CELL QUEST® program.

IFNγ was determined using the PBL population isolated by flow cytometric analysis. Two X $10^5$ PBL cells in 200 µl of serum-free medium (AIM-V®; Gibco/BRL, Life Technologies, Rockville, Md.) supplemented with 2% fetal bovine serum and $2 \times 10^{-5}$ MESH were plated in triplicate into 96 well plates and were incubated for 48 h with or without 10 µg/ml of the mitogen Concanavalin A (Con A) (Sigma Chemical Co, St. Louis, Mo.). Cell-free culture supernatants were collected and assayed for IFNγ using a capture ELISA (Mutwiri et al. 2000. Vaccine. In Press).

Among Groups 1, 2 and 3 animals, MCWE administration had no significant effect on total WBC counts, total T-lymphocytes/ml, total B-lymphocytes/ml and total monocytes/ml.

Figure 1B:
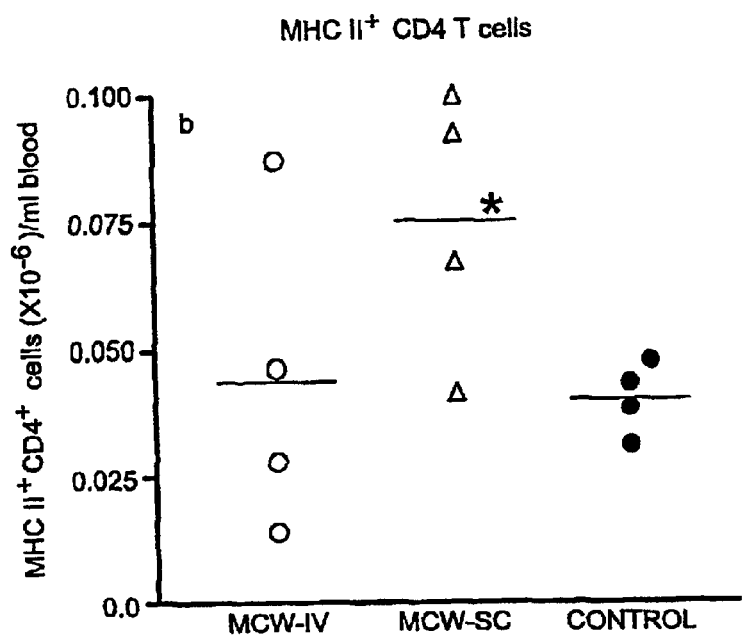

$CD25^+CD4^+$ T-lymphocytes were identified by flow cytometry as cells that co-labeled with CACT116A and IL-A11. MHC Class II$^+$CD4$^+$T-lymphocytes were identified by flow cytometry as cells that co-labeled with TH14B and IL-A11. Surface expression of CD25 and MIC Class II molecules is closely linked to CD4$^+$ T lymphocyte activation. That is, the number of CD4$^+$ T-lymphocytes expressing CD25 and MHC Class II is an indicator of immune activation. As shown in FIG. 1A, on day 4 post-MCWE treatment, clinically normal Group 2 animals (MCWE-SC) had more CD25$^+$CD4$^+$ T-lymphocytes/ml of blood than clinically normal Group 3 animals (saline-SC). As shown in FIG. 1B, on day 4 post-treatment, clinically normal Group 2 (MCWE-SC) animals had more MHC Class II$^+$CD4$^+$ T-lymphocytes/ml of blood than clinically normal Group 3 (saline-SC) animals.

Figure 2:
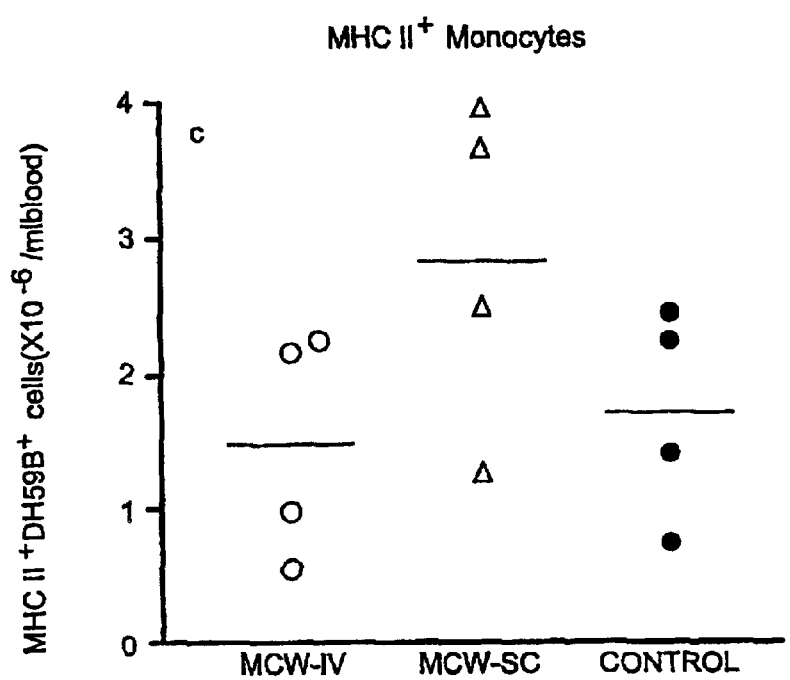
FIG. 2. MHC Class $II^+$ monocytes/ml in blood obtained on day 4 from calves treated within 24 h of birth (day 0) with MCWE-IV, MCWE-SC and saline-SC (control). Values are for individual animals and bars represent mean values for each group (n=4).

Monocytes in blood were identified by flow cytometry as cells that labeled with DH59B$^+$. MHC Class II$^+$ monocytes in blood were identified by flow cytometry as cells that co-labeled with TH14B and DH59B$^+$. Surface expression of MHC Class II molecules also is essential for monocytes to function as antigen presenting cells and the number of monocytes expressing MHC Class II is an indicator of the functional capacity of the immune system. As shown in FIG. 2, on day 4 post-treatment, clinically normal Group 2 (MCWE-SC) animals had more MHC Class II$^+$ monocytes/ml of blood than clinically normal Group 3 (saline-SC) animals.

Figure 3:
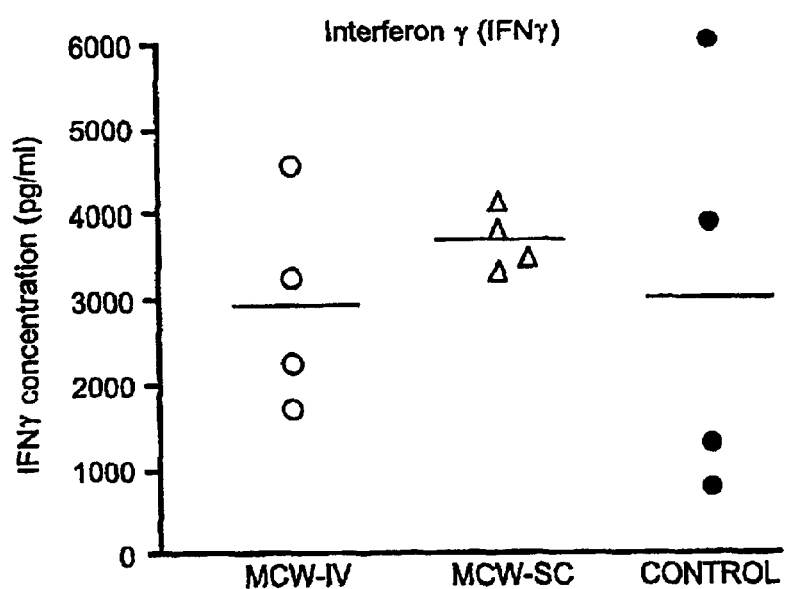
FIG. 3. INFγ production by WBCs obtained on day 4 from calves treated within 24 h of birth (day 0) with MCWE-IV, MCWE-SC and saline-SC (control). Values are for individual animals and bars represent mean values for each group (n=4).

INFγ production by WBCs was measured using the mitogen Con A in an in vitro stimulation assay. The cytokine INFγ plays a central role in regulating the immune system and activating effector cells that defend against intracellular pathogens. INFγ production by WBCs is an indicator of the capacity of the immune system to respond to infectious agents. As shown in FIG. 3, on day 4 post-treatment, WBCs from clinically normal Group 2 (MCWE-SC) animals showed a pronounced increase in INFγ production.

EXAMPLE 3
Enhancement of Production Performance in Calves by MCWE

On day 0, 400 hundred calves of domestic cows, less than 24 hours of age, were randomly divided into four equal groups (Groups 4–7). The calves were weighed, placed in individual hutches, fed twice daily with a grain-water milk replacer containing no antibiotics and subjected to the same routine ranch practices.

Within 24 hours of birth, Group 4 calves received 250 μg MCWE in 1 ml of emulsion IV, Group 5 calves received 250 μg MCWE in 1 ml of emulsion IM, Group 6 calves received 250 μg MCWE in 1 ml of emulsion SC and Group 7 calves received no MCWE (control).

Each animal was observed twice daily for changes in appetite, hydration and signs of sickness. The mortality, sick days and treatment costs for each animal were noted. After 71–78 days, each animal was weighed and the average daily weight gain (ADG) was calculated as follows:

$$\frac{\text{lbs on day 71--78} - \text{lbs on day 0}}{\text{lbs on day 71--78}}$$

Figure 4:
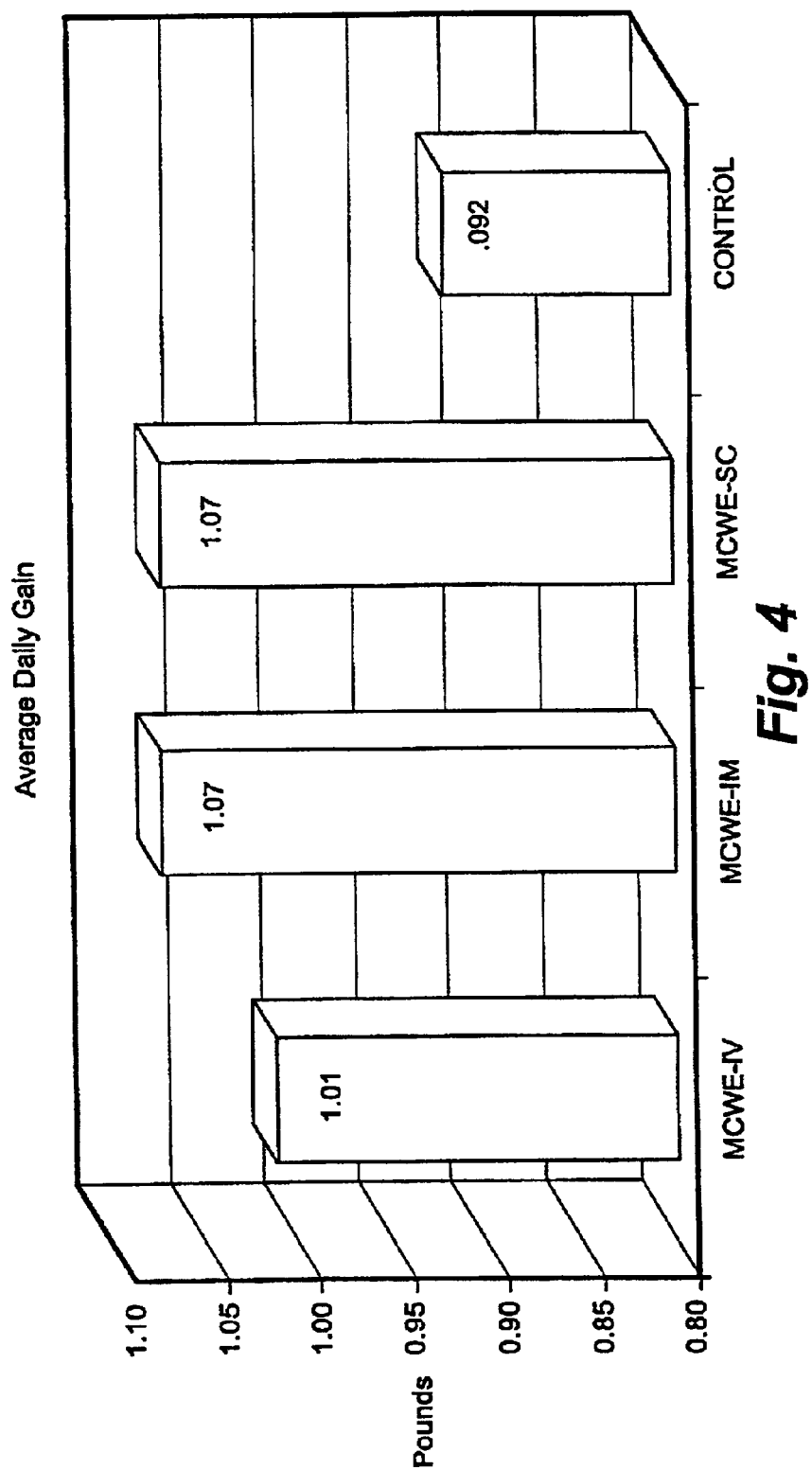
FIG. 4. Average daily weight gain among calves treated, within 24 h of birth (day 0), with MCWE-IV, MCWE-IM, MCWE-SC and no MCWE (control).

The results of treatment on ADG for Groups 4–7 are shown in in Table 3 and in FIG. 4. Only those animals for whom data was complete on the final day of the study were included in the calculations. Each group began with 100 animals. At the end of the study, data were complete for 91 animals in Group 4 (MCWE-IV), 89 animals in Group 5 (MCWE-IM), 93 animals in Group 6 (MCWE-SC) and 96 animals in Group 7 (control).

TABLE 3

Production performance of newborn calves

| GROUP | NUMBER OF ANIMALS | AVERAGE WEIGHT (LBS) DAY 0 | AVERAGE WEIGHT (LBS) DAY 71–78 | AVERAGE GAIN (LBS) | ADG (LBS) |
| --- | --- | --- | --- | --- | --- |
| 4 (IV) | 91 | 89.38 | 158.27 | 76.76 | 1.01 |
| 5 (IM) | 89 | 91.98 | 162.54 | 80.58 | 1.07 |
| 6 (SC) | 93 | 86.91 | 162.34 | 81.08 | 1.07 |
| 7 | 96 | 87.39 | 153.28 | 69.54 | 0.92 |

ADG, was enhanced significantly ($p<0.02$) in MCWE treated animals (Groups 4–6) as compared to control animals (Group 7). MCWE treated animals gained approximately 0.1 lb/day in excess of control animals.

Figure 5:
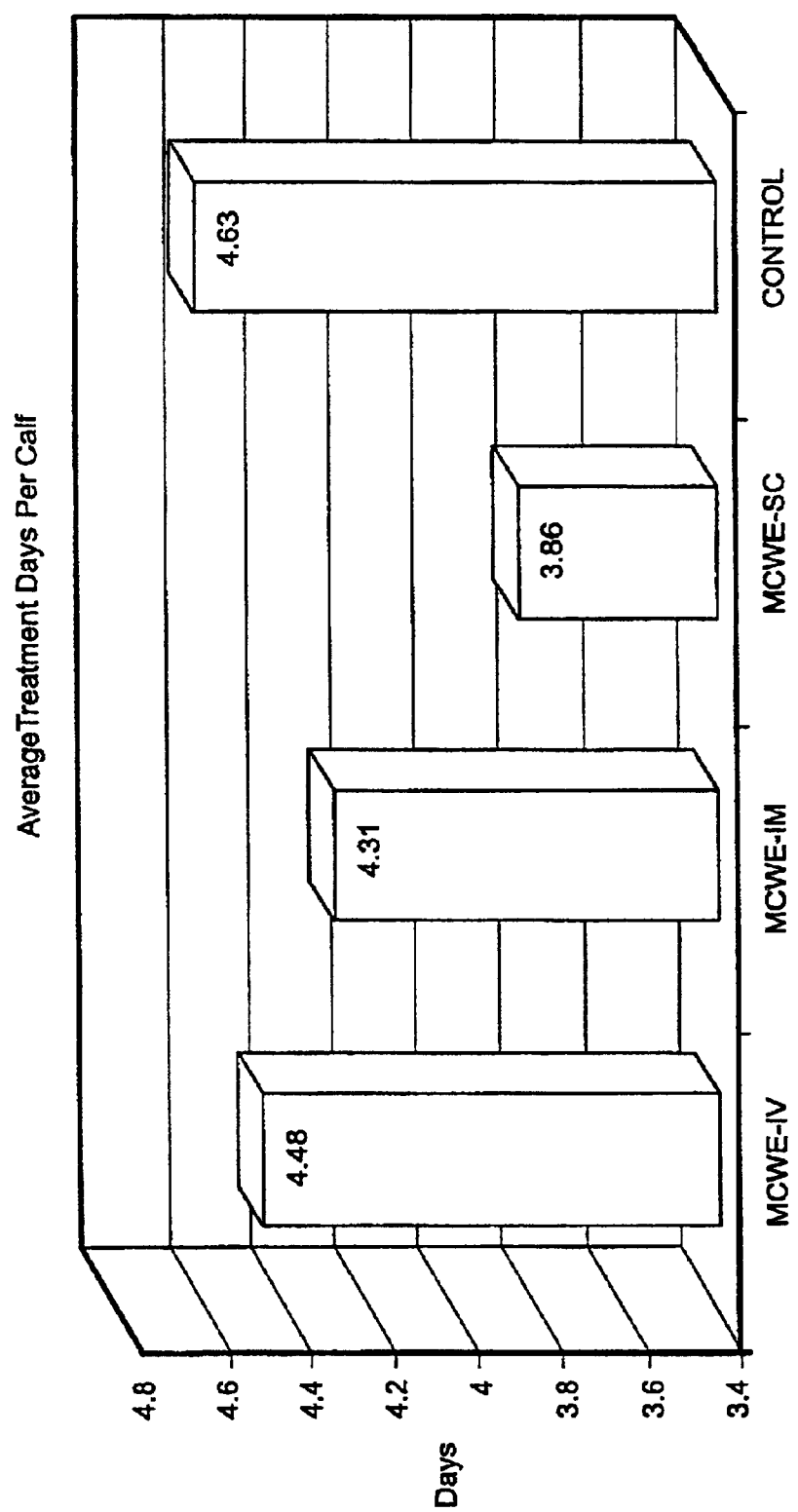
FIG. 5. Average number of days, during a 71–78 day period, that treatment was necessary to maintain the health of animals who, within 24 h of birth (day 0), received MCWE-IV, MCWE-IM, MCWE-SC or no MCWE (control).
Figure 6:
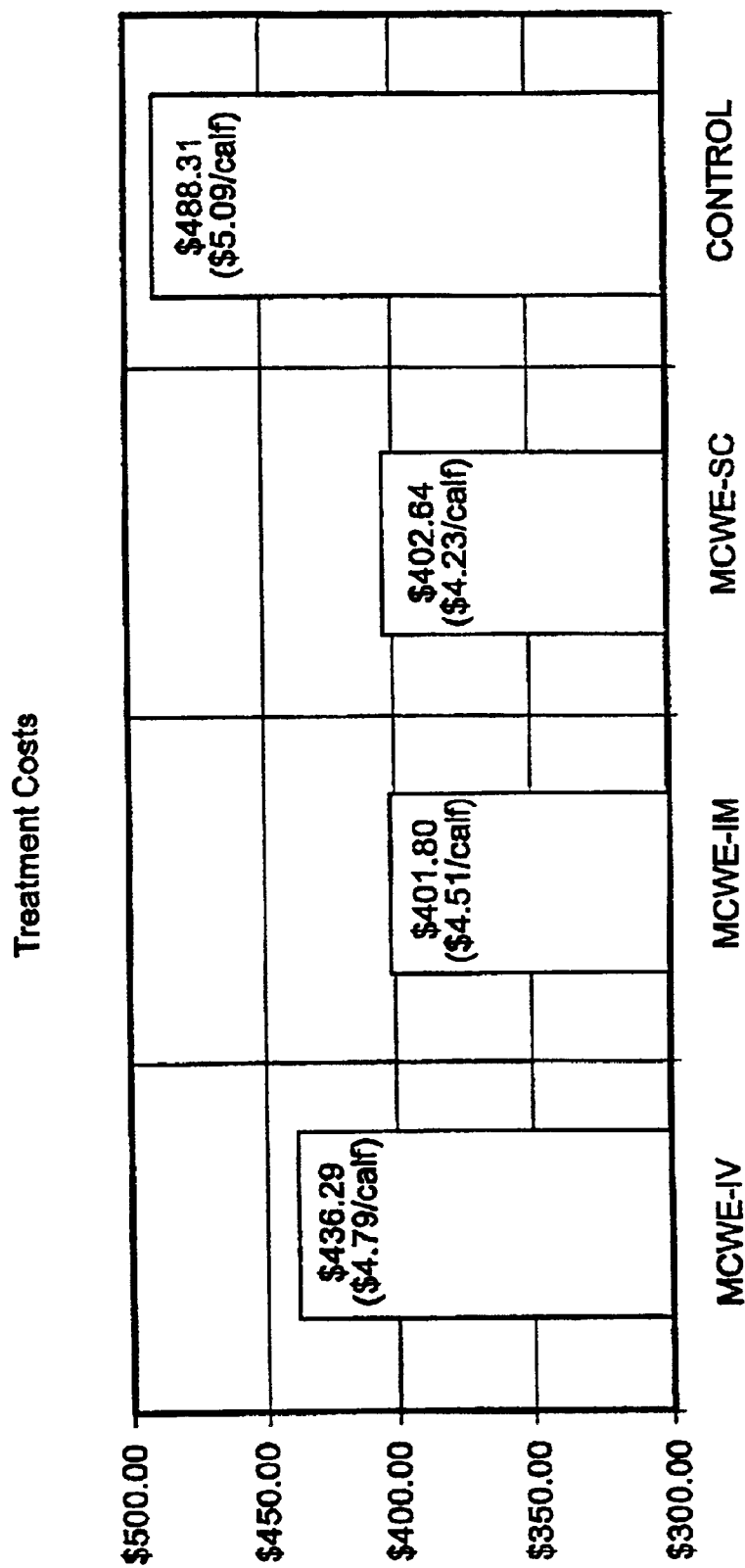
FIG. 6. Costs, during a 71–78 day period, associated with the treatments necessary to maintain the health of animals who, within 24 h of birth (day 0), received MCWE-IV, MCWE-IM, MCWE-SC or no MCWE (control).

The average number of days of treatment and the costs of treatment necessary to maintain the health of the animals were compared over a 71–78 day period. FIG. 5 shows that the average number of treatment days was higher for Group 7 (control) animals than for Groups 4–6 (MCWE treated) animals. FIG. 6 shows that treatment costs over the 71 to 78 day period were higher for Group 7 (control) animals than for Groups 4–6 (MCWE treated) animals.

EXAMPLE 4
Enhancement of Production Performance in Pigs by MCWE

On day 0, piglets from domestic sows, less than 24 hours of age, are randomly divided into two equal groups (Groups 8 & 9). The piglets are weighed, fed twice daily and subjected to the same routine ranch practices. Within 24 hours of birth, each Group 8 piglet receives MCWE emulsion SC. Group 9 piglets receive no MCWE (control). Each piglet is observed for changes in appetite, hydration and signs of sickness. On day 30 the animals are weighed and the ADG for each animal is calculated. Mortality, sick days and treatment costs for each animal during the 30 days period also are determined. At the end of the study period, Group 8 (MCWE treated) animals have better ADG, lower mortality, fewer sick days and less treatment costs than Group 9 (control) animals.

EXAMPLE 5
Enhancement of Production Performance in Chickens by MCWE

On day 0, chicks from the common domestic fowl, less than 24 hours of age, are randomly divided into two equal groups (Groups 10 & 11). The chicks are weighed, fed and subjected to the same routine ranch practices. Within 24 hours of birth, each chick in Group 10 receives MCWE emulsion orally. The chicks in Group 11 receive no MCWE (control). Each chick is observed for changes in appetite, hydration and signs of sickness. On day 15 the chicks are weighed and the ADG for each bird is calculated. Mortality, sick days and treatment costs for each bird also are determined. At the end of the study period, Group 10 (MCWE treated) chicks have better ADG, lower mortality, fewer sick days and less treatment costs than Group 11 (control) chicks.

EXAMPLE 6
Enhancement of Production Performance in Sheep by MCWE

On day 0, lambs from domestic sheep, less than 24 hours of age, are randomly divided into two equal groups (Groups 12 & 13). The lambs are weighed, fed and subjected to the same routine ranch practices. Within 24 hours of birth, each lamb in Group 12 receives MCWE emulsion SC. The lambs in Group 13 receive no MCWE. Each lamb is observed for changes in appetite, hydration and signs of sickness. On day 40 the lambs are weighed and the ADG for each lamb is calculated. Mortality, sick days and treatment costs for each lamb also are determined. At the end of the study period, Group 12 (MCWE treated) lambs have better ADG, lower mortality, fewer sick days and less treatment costs than Group 13 (control) lambs.

It should be understood, of course, that the foregoing relates only to preferred embodiments of the present invention and that numerous modifications or alterations may be made therein without departing from the spirit and the scope of the invention as set forth in the appended claims.

What is claimed is:

1. A method, comprising administering to an animal between 1 hour and 28 days of age, an amount of a mycobacterial cell wall extract, wherein the amount is effective to activate the immune system of the animal, wherein the mycobacterial cell wall extract contains oil.

2. The method of claim 1, wherein the administration to the animal occurs between 1 hour and 4 days of age.

3. The method of claim 1, wherein the administration to the animal occurs between 1 hour and 24 hours of age.

4. The method of claim 1, wherein the mycobacterial cell wall extract is prepared from family Mycobacteriaceae, genus *Mycobacterium*, or species *Mycobacterium phlei*.

5. The method of claim 1, wherein activation of the immune system comprises activation of white blood cells.

6. The method of claim 5, wherein the white blood cells are group T-lymphocytes or monocytes.

7. The method of claim 6, wherein the T-lymphocytes are $CD4^+$ T lymphocytes.

8. The method of claim 7, wherein the $CD4^+$ T lymphocytes are $CD25^+CD4^+$ T lymphocytes or MHC Class $II^+CD4^+$ T lymphocytes.

9. The method of claim 6, wherein the monocytes are MHC Class $II^+$ monocytes.

10. The method of claim 5, wherein the activated white blood cells display enhanced production of IFN-γ in response to a stimulus.

11. The method of claim 1, wherein the animal is a mammal, bird, fish, amphibian or crustacean.

12. The method of claim 1, wherein the animal is domestic food animal.

13. The method of claim 12, wherein the domestic food animal is a calf, a chick, a piglet, a kid, a fawn or a lamb.

14. The method of claim 12, wherein the domestic food animal is a calf of a domestic cow.

15. The method of claim 12, wherein the domestic food animal is a chick of a domestic fowl.

16. The method of claim 1, wherein the mycobacterial cell wall extract is combined with a pharmaceutically acceptable carrier.

17. The method of claim 1, wherein the administration is subcutaneous, intravenous, intramuscular, intraperitoneal or oral.

18. The method of claim 1, wherein the amount of the mycobacterial cell wall extract administered to the animal is from about 0.001 μg per kg to about 600 μg per kg per dose.

19. The method of claim 1, wherein the amount of the mycobacterial cell wall extract administered to the animal is from about 0.01 μg per kg to about 400 μg per kg per dose.

20. The method of claim 1, wherein the amount of the mycobacterial cell wall extract administered to the animal is from about 0.1 μg per kg to about 200 μg per kg per dose.

21. A method, comprising administering to an animal between 1 hour and 28 days of age, an amount of a mycobacterial cell wall extract, wherein the amount is effective to enhance production performance of the animal.

22. The method of claim 21, wherein the administration to the animal occurs between 1 hour and 4 days of age.

23. The method of claim 21, wherein the administration to the animal occurs between 1 hour and 24 hours of age.

24. The method of claim 21, wherein the mycobacterial cell wall extract is prepared from family Mycobacteriaceae, genus *Mycobacterium*, or species *Mycobacterium phlei*.

25. The method of claim 21, wherein the enhancement of production performance is an increase in the average daily weight gain of the animal or an increase in efficiency of feed use.

26. The method of claim 21, wherein the enhancement of production performance is a decrease in the mortality of the animal, a decrease in the number of treatment days necessary to maintain the health of the animal, a decrease in the cost of treatment necessary to maintain the health of the animal, or any combination thereof.

27. The method of claim 21, wherein the animal is a mammal, bird, fish, amphibian or crustacean.

28. The method of claim 21, wherein the animal is domestic food animal.

29. The method of claim 28, wherein the domestic food animal is a calf, a chick, a piglet, a kid, a fawn or a lamb.

30. The method of claim 28, wherein the domestic food animal is a calf of a domestic cow.

31. The method of claim 28, wherein the domestic food animal is a chick of a domestic fowl.

32. The method of claim 21, wherein the mycobacterial cell wall extract is combined with a pharmaceutically acceptable carrier.

33. The method of claim 21, wherein the administration is subcutaneous, intravenous, intramuscular, intraperitoneal or oral.

34. The method of claim 21, wherein the amount of the mycobacterial cell wall extract administered to the animal is from about 0.001 μg per kg to about 600 μg per kg per dose.

35. The method of claim 21, wherein the amount of the mycobacterial cell wall extract administered to the animal is from about 0.01 μg per kg to about 400 μg per kg per dose.

36. The method of claim 21, wherein the amount of the mycobacterial cell wall extract administered to the animal is from about 0.1 μg per kg to about 200 μg per kg per dose.

* * * * *